United States Patent [19]

Agee et al.

[11] Patent Number: 4,611,586

[45] Date of Patent: Sep. 16, 1986

[54] ARTICULATED COLLES' FRACTURE SPLINT

[75] Inventors: John M. Agee, 3980 Bartley Dr., Sacramento, Calif. 95822; Francis C. King, Shingle Springs, Calif.

[73] Assignee: John M. Agee, Sacramento, Calif.

[21] Appl. No.: 539,766

[22] Filed: Oct. 6, 1983

[51] Int. Cl.[4] .............................................. A61F 5/04
[52] U.S. Cl. ............................ 128/92 A; 128/92 EB
[58] Field of Search ............... 128/92 A, 92 R, 84 R, 128/84 B, 84 C, 88

[56] References Cited

U.S. PATENT DOCUMENTS

| | | | |
|---|---|---|---|
| 1,789,060 | 1/1931 | Weisenbach | 128/92 A |
| 2,333,033 | 10/1943 | Mraz | 128/92 A |
| 2,371,519 | 3/1945 | Haynes | 128/92 A |
| 2,393,982 | 2/1946 | Giesen | 128/92 A |
| 2,435,850 | 2/1948 | Siebrandt | 128/92 A |
| 4,135,505 | 1/1979 | Day | 128/92 A |
| 4,271,832 | 6/1981 | Evans et al. | 128/92 A |
| 4,299,212 | 11/1981 | Goudfrooy | 128/92 A |
| 4,312,336 | 1/1982 | Danieletto et al. | 128/92 A |
| 4,338,927 | 7/1982 | Volkov et al. | 128/92 A |
| 4,488,542 | 12/1984 | Helland | 128/92 A |

FOREIGN PATENT DOCUMENTS

| | | | |
|---|---|---|---|
| 2437752 | 2/1976 | Fed. Rep. of Germany | 128/92 A |
| 2745504 | 4/1979 | Fed. Rep. of Germany | 128/92 A |
| 2086231 | 5/1982 | United Kingdom | 128/92 A |

Primary Examiner—Gene Mancene
Assistant Examiner—C. W. Shedd
Attorney, Agent, or Firm—Townsend and Townsend

[57] ABSTRACT

A splint, for setting a Colles' fracture, formed from a pair of relatively shiftable elements, one of which is an elongated support element having a traveling block shiftable along the length thereof, the second element being pivotally mounted on the first element. The pivotal axis of the two relatively movable elements is aligned with the rotational axis of the fracture site itself, specifically the distal radial-ulnar joint, the joint between the radius and ulna at the level of the wrist. The travelling block is adjusted by a first worm and rack, and the angular adjustment between the pivoted elements is achieved with a second worm and a worm gear, the traveling block and the second element each having holes for receiving bone pins which extend into the radius proximal to the fracture and the metacarpal bones distal to the fracture. The first element is preferably made of plastic and transparent to x-rays. With the traveling block shiftable along the first element, distraction of the radius restores length to the same; a second selective adjustment rotates the first element relative to the second element and, in so doing, carries the hand, wrist and distal fragment through the same axis about which the fracture originally evolved and thereby improves both rotational and appositional alignment at the fracture site. A modified traveling block permits moving the hand and thereby the wrist and distal fragment in a radial and ulnar direction by rotating a screw having a wing nut thereon. The modified traveling block also allows selective extension and flexion of the wrist.

44 Claims, 22 Drawing Figures

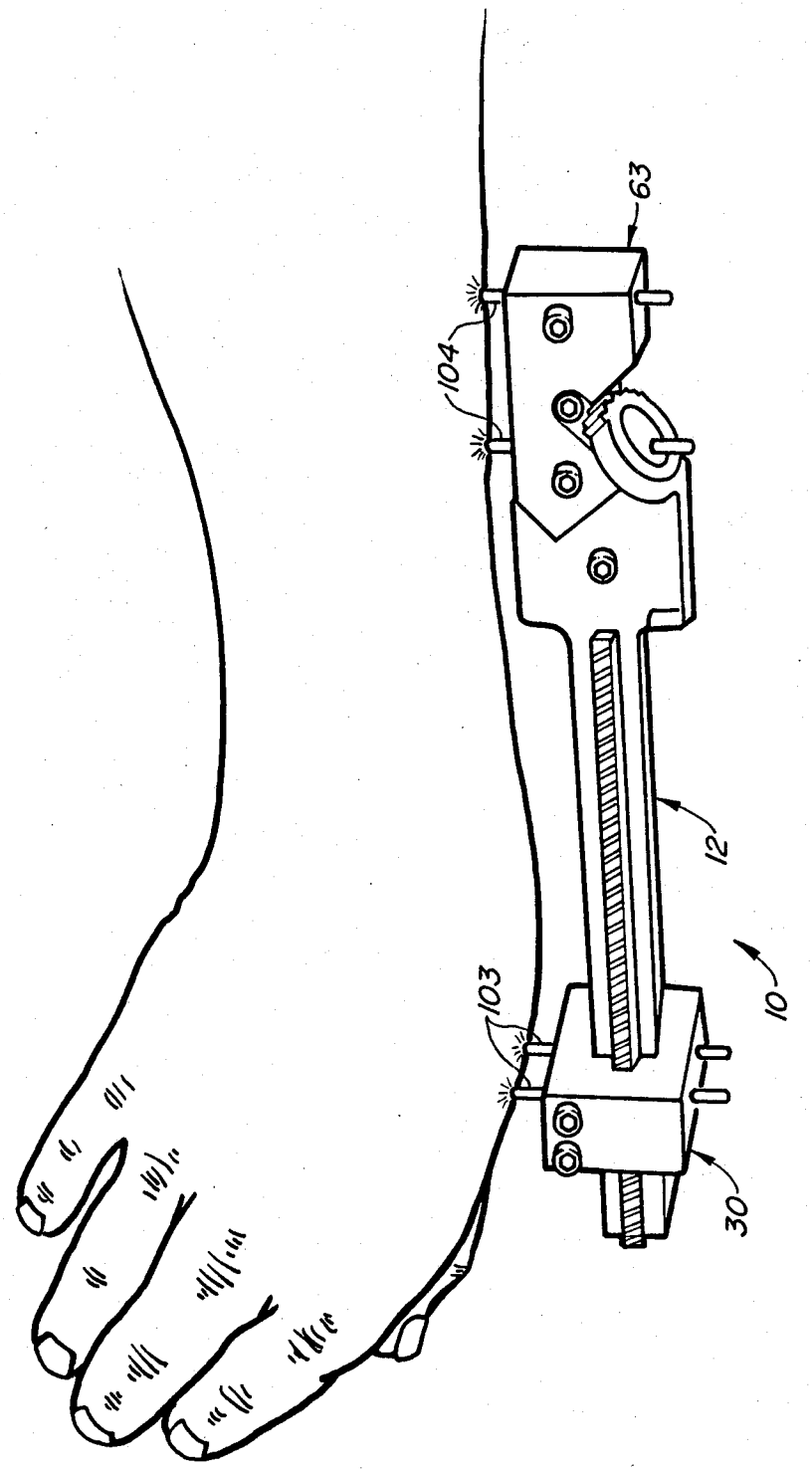

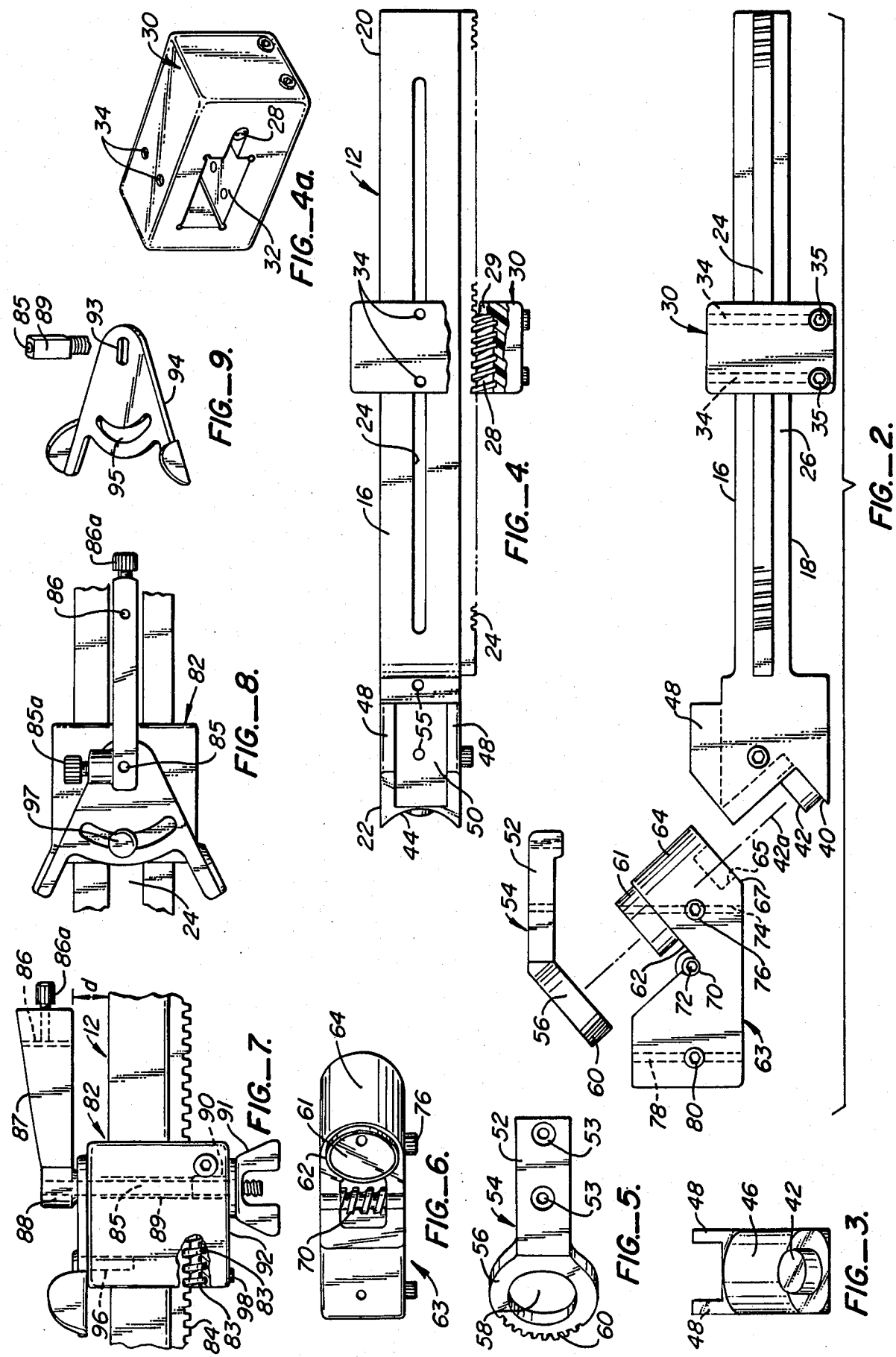

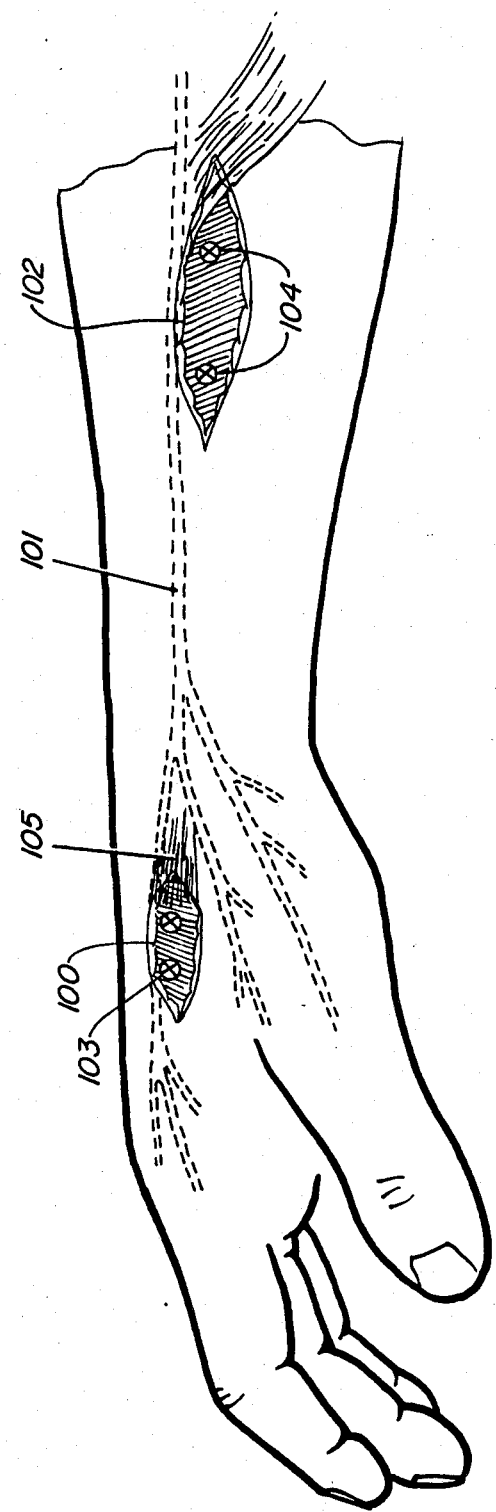
FIG._10.

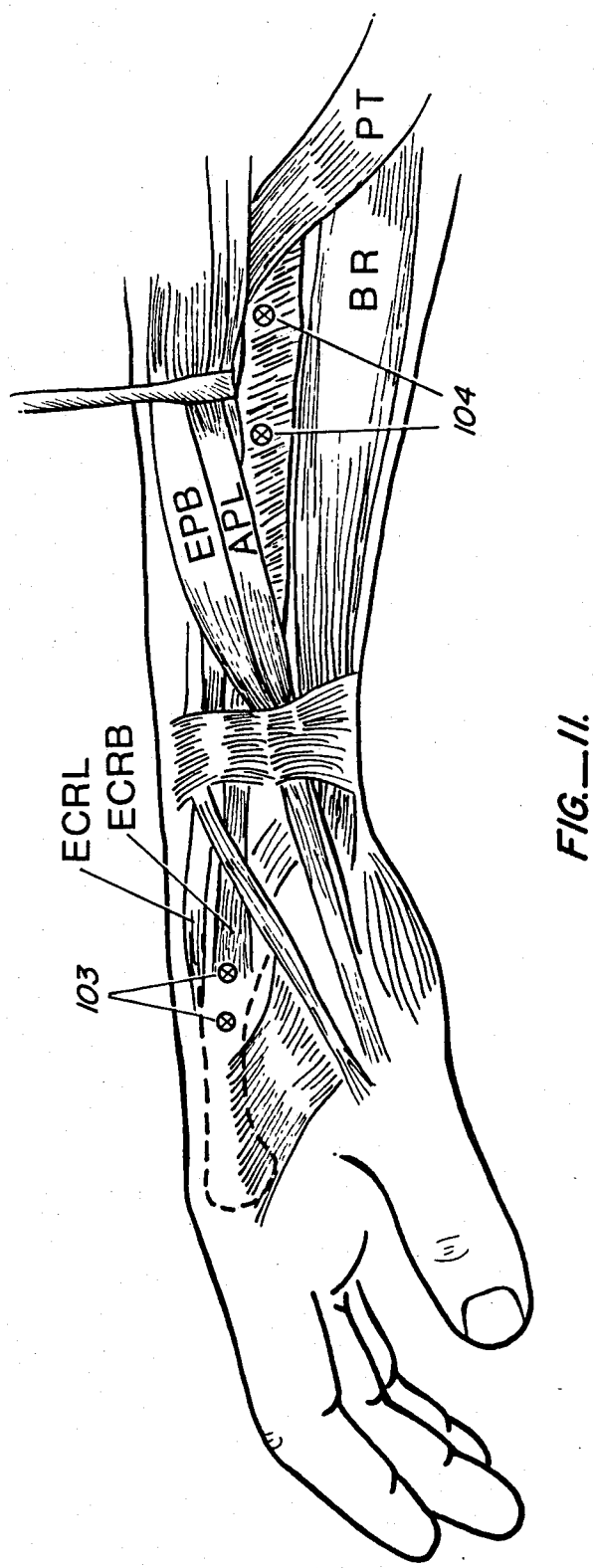
FIG._11.

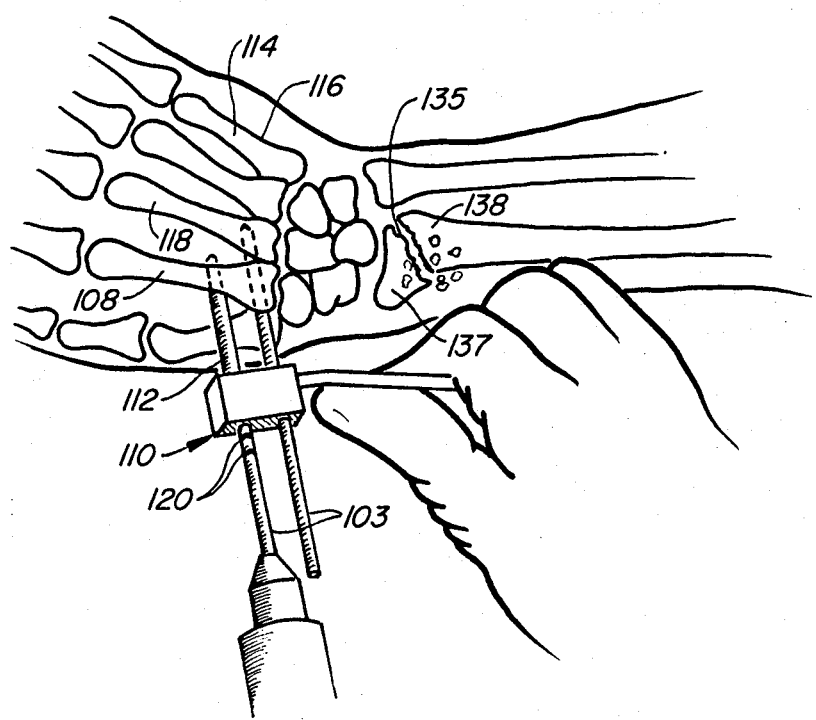
FIG._12.

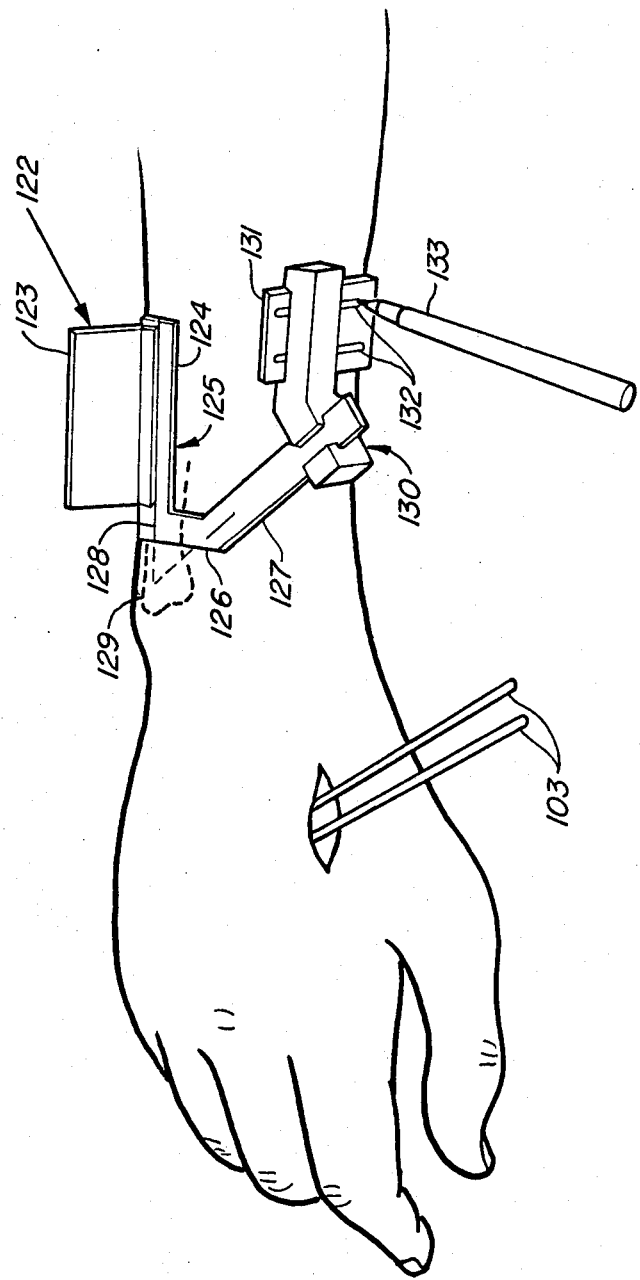

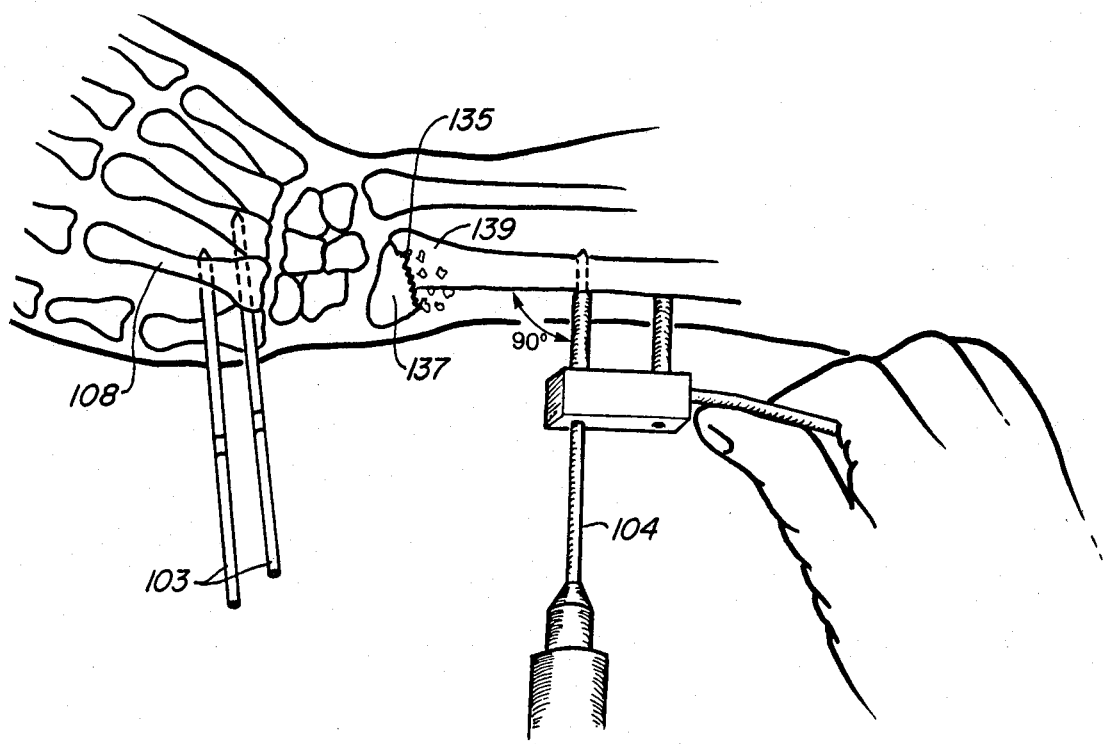
FIG.—14.

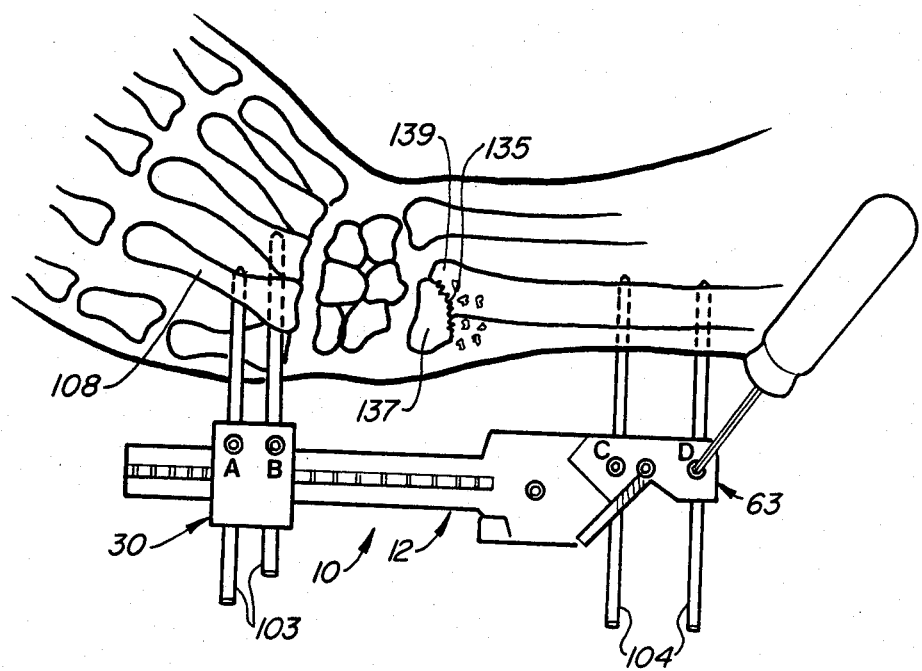
FIG._15.

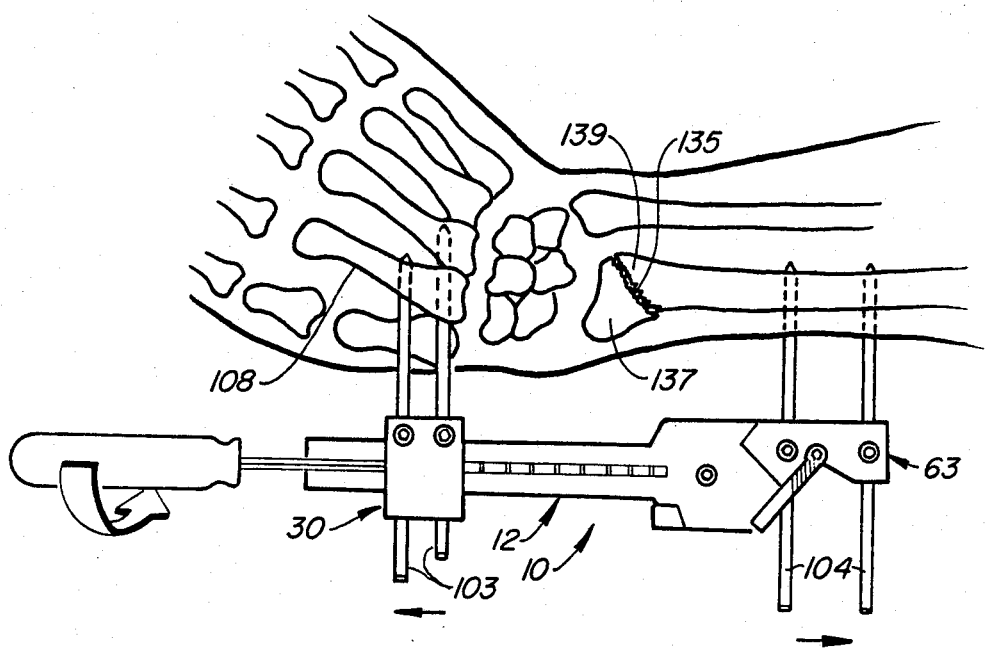
FIG._16.

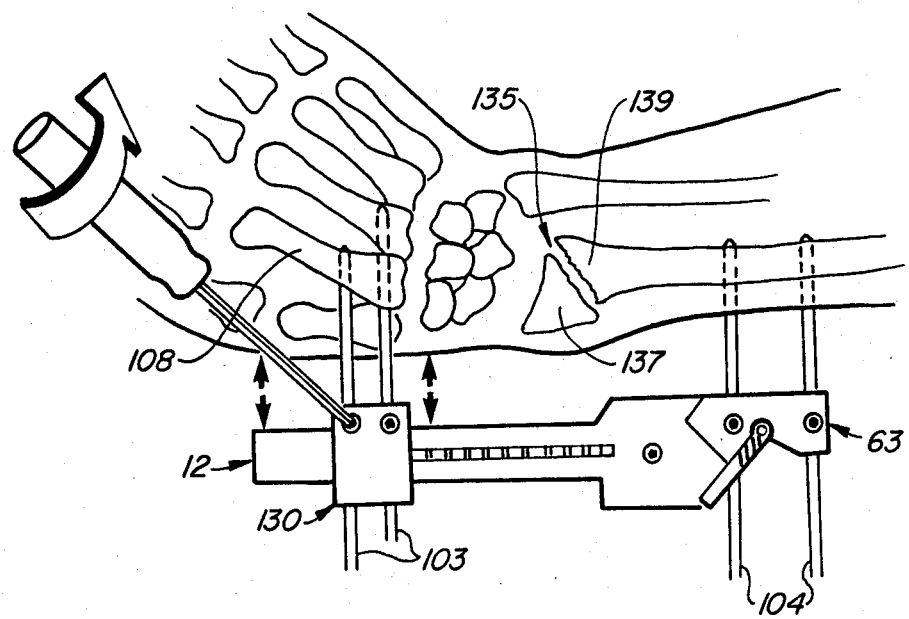
FIG._17.

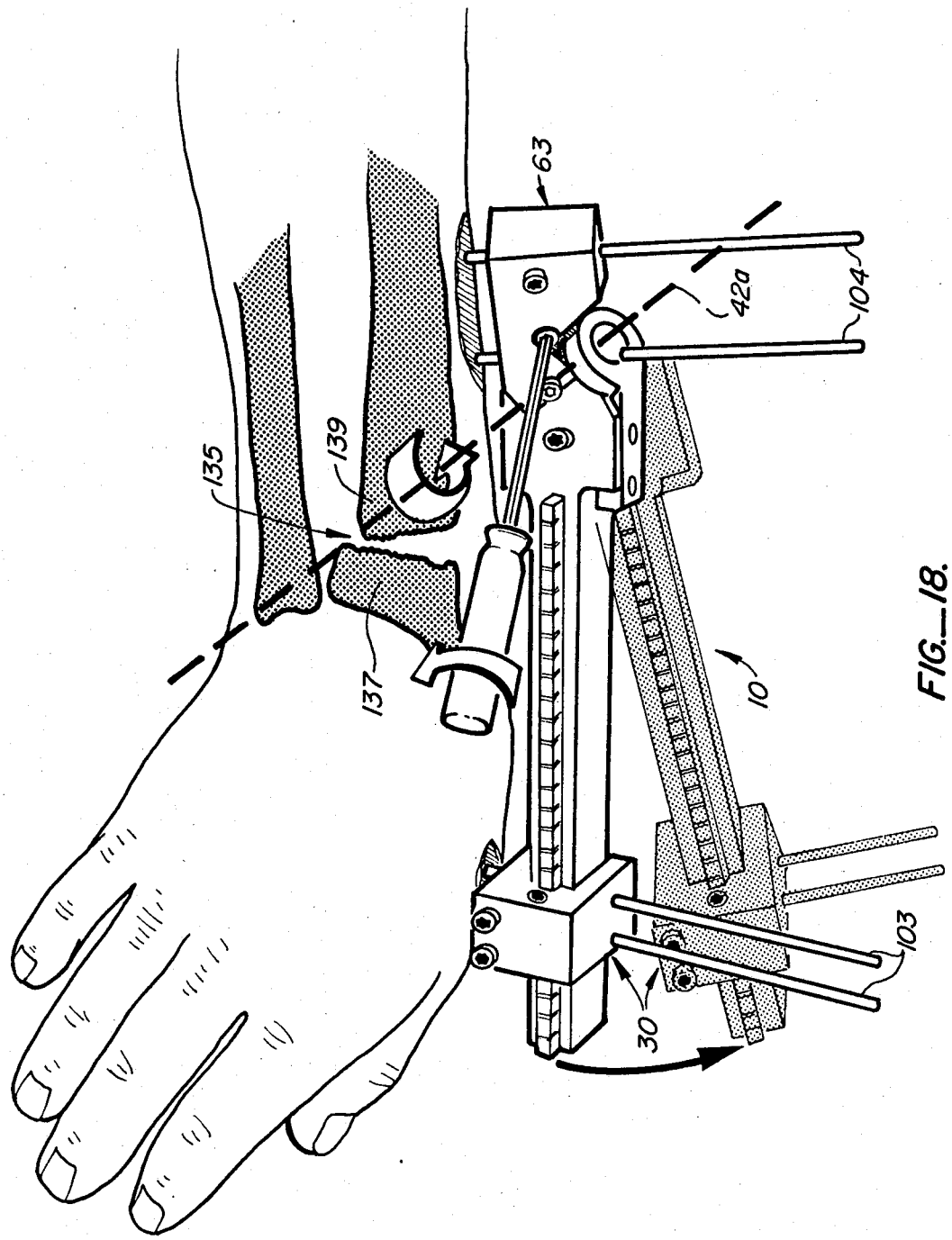
FIG._18.

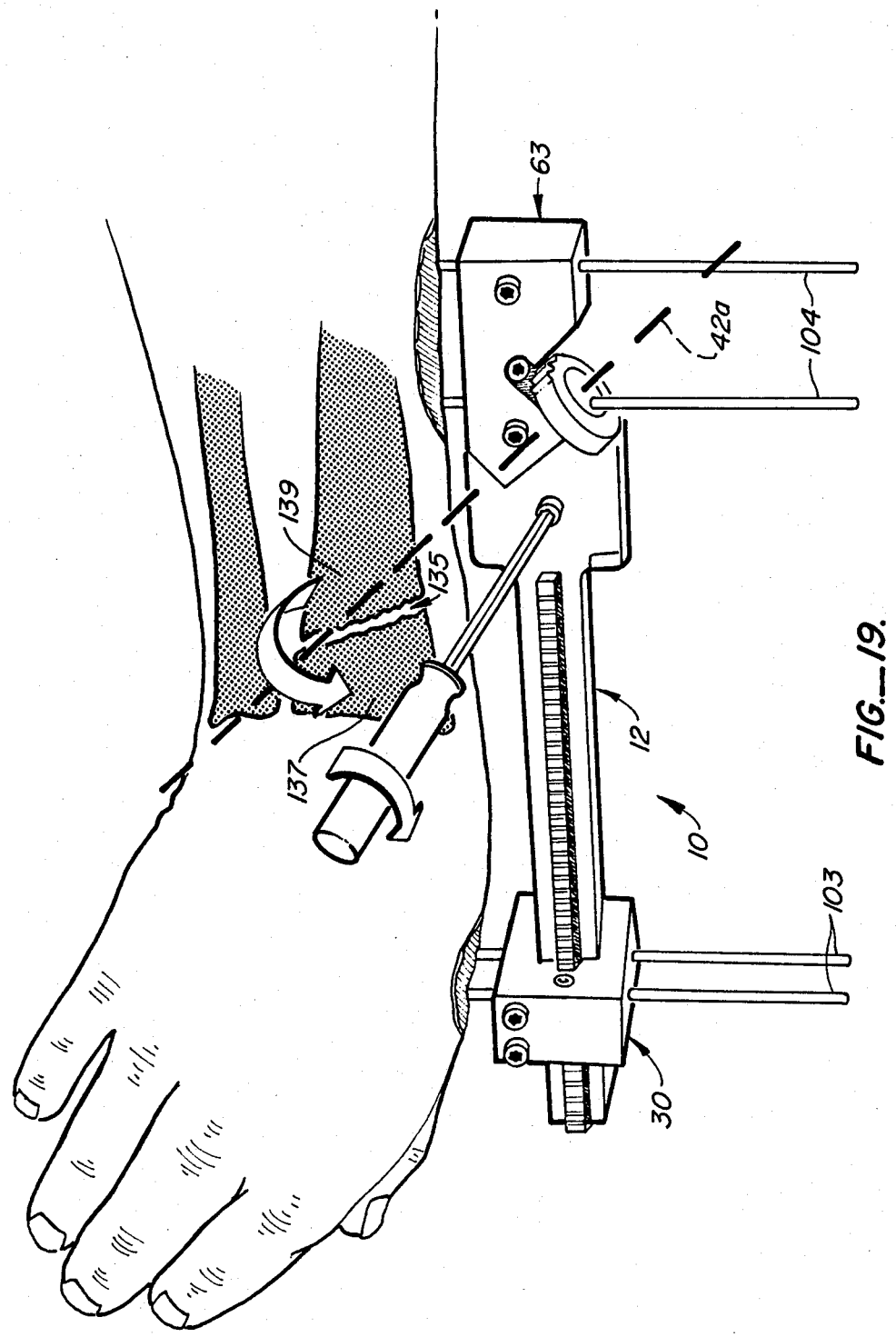
FIG._19.

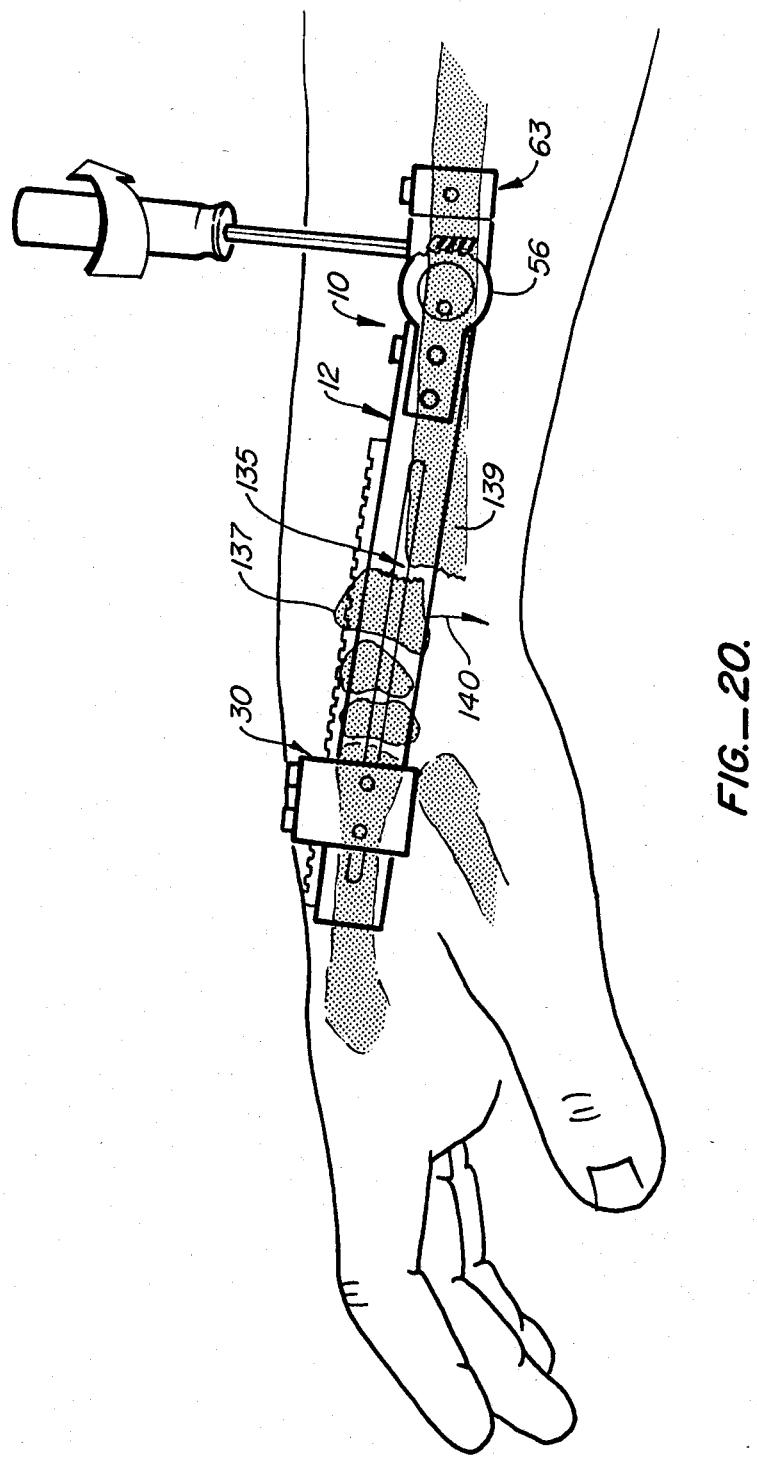
FIG.—20.

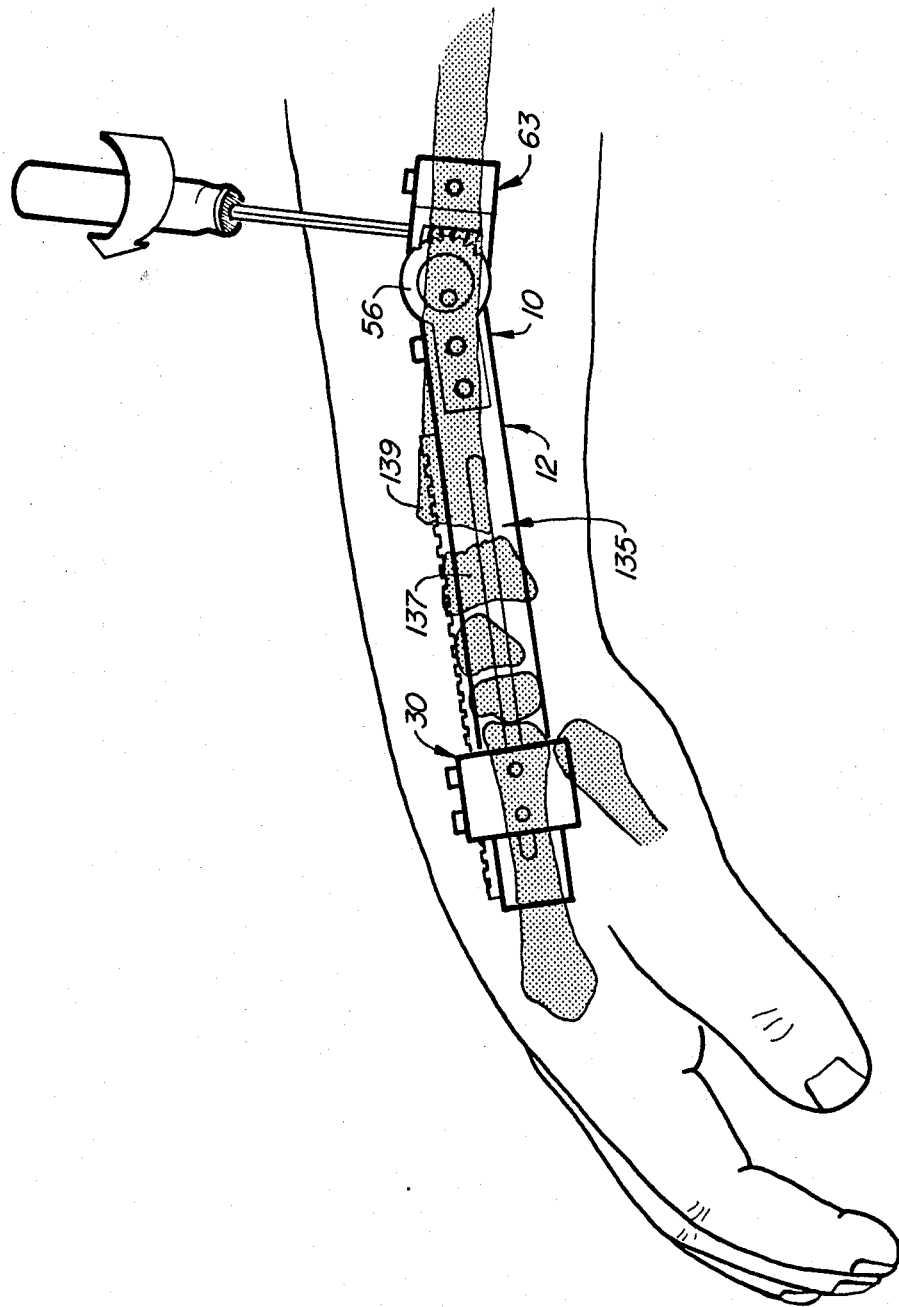
FIG._21.

ARTICULATED COLLES' FRACTURE SPLINT

This invention relates to splint for fractures of the human skeleton and, more particularly, to a splint for use with fractures of the distal radius and/or wrist joint.

BACKGROUND OF THE INVENTION

A number of different techniques have been devised and used to provide for reduction of a displaced fracture and for the maintenance of the same during fracture healing. For the most part, the devices used to set the fracture of the distal radius in the forearm have been unsatisfactory for one or more reasons. In particular, external fixators (hereinafter referred to as splints) which have been known and used in the past have not been properly designed to provide selective and continuously adjustable degrees of distraction across the fracture site by means which allows for independent adjustment for both appositional and rotational alignment of the same fracture so as to provide the capability of easily returning the distal and proximal fragments to there proper location and to hold them in such locations until the fracture has healed.

Another drawback with the use of conventional splints used to treat a fracture is the fact that such splints are comprised of metallic parts, such as rods, screws and pin-holding members which span the fracture site. Such metallic parts are opaque to x-rays and do not permit viewing of all aspects of a fracture site in x-ray photographs.

The third major drawback with the use of conventional splints for treating a fracture is in the design deficiencies which prevent the selective displacement of the hand and thereby the wrist and distal fragment of the radius in a radial and ulnar direction while isolating this aspect of the fracture reduction from the other three aspects of the fracture reduction, namely, apposition in a dorsal-palmar direction, rotational alignment, and length or degree of distraction. Thus, with conventional splints, it is not possible to manipulate the fracture reduction in a radial and ulnar direction without losing the beneficial adjustments provided by the other three aspects of fracture reduction.

A further drawback, associated with conventional splints is that they do not allow for selective extension and flexion of the wrist joint itself. Such extension and flexion can frequently facilitate fracture reduction and/or minimize the risks of extensor tendon "overpull" through wrist extension. Specifically, wrist extension relaxes the tension on the finger extensor tendons and thereby minimizes the risk of producing a stiff hand by allowing more flexion of the metacorpophalangeal joints of the fingers.

A prior disclosure relating to a Colles' type fracture splint is U.S. patent application Ser. No. 321,150, filed Nov. 13, 1981 by John M. Agee. This disclosure describes two embodiments of a fracture splint, one of which provides distraction of the distal and proximal bone fragments relative to a fracture site and the other being designed to project an axis from its two major moveable parts that becomes coincident with the rotational axis about which most Colles' type fractures typically rotate. Both of these embodiments have metallic parts which render it difficult to provide x-ray photographs of the fracture site with the splint in place. Moreover, neither embodiment allows for selective adjustment of appositional alignment as appreciated from the anterior-posterior x-ray view, i.e., adjustments of the radioulnar alignment of the fracture. Further, neither embodiment allows for wrist flexion and extension.

Because of the foregoing drawbacks, improvements in a Colles' type splint are needed to provide for proper treatment of Colles' type fractures.

SUMMARY OF THE INVENTION

The present invention satisfies the aforesaid need by providing an improved splint especially suitable for use in treating a Colles' type fracture. The splint of the present invention includes an elongated distal element having a traveling block shiftable along the length thereof, the traveling block having means for mounting one or a pair of distal pins thereon, the pins being insertable into and frequently through the metacarpal of the index finger to secure skeletal fixation on the distal side of the fracture site.

A proximal element is pivotally mounted on the proximal end of the distal element and is provided with a pair of pin-receiving holes therethrough. An improved adjustment means between the distal and proximal elements effects pivotal movement of these two elements relative to each other. Such adjustment means is preferably in the form of a worm and worm gear configured to allow one of the pins to pass through the worm gear and to be inserted into the proximal fragment without interference with the worm gear itself. A worm and rack is preferably used to move the traveling block relative to the distal element.

Another aspect of the splint of the present invention is the fact that the distal element can be made of rigid, high strength plastic substantially transparent to x-rays to allow x-ray photographs to be taken through the splint. This will permit viewing of the fracture site at all angles in an x-ray photograph. This feature improves the quality of assessment of alignment and thereby enhances the healing rate.

A further improvement of the splint of the present invention lies in the fact that the splint is constructed to allow the distal element of the splint to carry the hand, the wrist and the distal fragment of the fractured radius about an arc with respect to the proximal element of the splint when the proximal element is attached to the radius on the proximal side of the fracture site. The main biomechanical contribution of the splint of the present invention is the way in which the splint biomechanically complements the pathomechanics of a Colles' type fracture. Thus, the splint biomechanically complements a Colles' type fracture by reducing the fracture displacement about the same axis through which the fragments are displaced at the time of the injury. Thus, by using the splint of the present invention, the splint can reverse the deformity, thereby achieving fracture reduction selectively and with control.

In a modified version of the traveling block on the distal element, the splint has the capability of permitting selective movement of the hand and thereby the wrist and distal fragment of the radius in a radial and ulnar direction by use of a simple adjustment device, such as a wing nut, which can be moved or rotated on the modified traveling block. Moreover, the modified traveling block is designed to allow for selective extension and flexion of the wrist while permitting distracting forces to restore proper length to the radius bone.

A key feature of the splint of the present invention is the means thereon which allows selective improvement of the fracture in one plane and/or about one axis of its evolution without substantially altering the alignment in another plane and/or axis. The adjustments are made in a simple manner and in a rather selective fashion by simply manipulating an adjustment device, such as by turning a screw, as opposed to most, if not all, of the currently available fracture splints which are like "erector sets", i.e., if the adjustment is not correct as indicated on an x-ray photograph, a screw or universal joint is loosened and several degrees of freedom are available to the fracture site. Thus, if the fracture reduction is slightly out of adjustment, such as from front to back or anterior posterior, a surgeon might be reluctant to try to improve it by manipulating the adjustment means on a conventional splint. The reason for this is that, once the "erector set" mechanism of a conventional splint is loosened, improvement in the alignment in one plane might occur at the expense of alignment in one or more other planes.

Another feature of the splint of the present invention is that it relates to the specific anatomy of a problem fracture. The splint allows for radial and ulnar displacement of the hand on the forearm and thereby displaces the fracture in radial and ulnar directions.

Another key feature of the present invention is that, using the splint of the present invention, a surgeon can selectively displace the hand and thereby the wrist and distal fragment of the radius in a raidal and ulnar direction by means which isolates that aspect of the fracture reduction from the other three aspects of fracture reduction, namely, apposition in a dorsalpalmar direction, rotational alignment, and length or degree of distraction. In this respect, it is desirable to permit manipulation of the fracture reduction in a radial and ulnar direction without losing the beneficial effects gained by adjustments of the splint in the other axis. In addition to the foregoing, the splint of the present invention allows for selective extension and flexion of the wrist joint to facilitate fracture reduction.

The primary object of this invention is to provide an improved splint for use in selectively reducing the displacement in a Colles' type fracture wherein the splint is configured to transmit distracting forces into the skeleton proximal and distal to the fracture site while simultaneously allowing for rotational and appositional alignment of the distal and proximal fragments, all of which can be accomplished quickly and easily by mechanical adjustments that improvement alignment in one plane and/or about one axis without substantially interfering with alignment in the remaining planes and/or axes.

Another object of the present invention is to provide a splint of the type described wherein the distal portion of the splint can be formed of plastic material transparent to x-rays, yet the splint has high strength characteristics so that x-ray photographs of the fracture site can be made with the splint in place and without affecting adjustments of the splint.

Another object to the present invention is to provide a splint of the type described wherein the splint has a traveling block on the distal portion thereof, with the traveling block being designed to permit selective movement of the hand and thereby the distal fragment in a radial and ulnar direction by a simple adjustment yet the same traveling block allows for selective extension and flexion of the wrist.

Other object of this invention will become apparent as the following specifications progresses, reference being had to the accompanying drawings for an illustration of several embodiments of the invention.

IN THE DRAWINGS

FIG. 1 is a perspective view of an improved fracture splint of the present invention secured in an operative position on the radial aspect of the forearm;

FIG. 2 is a dorsal elevational view of the fracture splint of FIG. 1, parts being separated from each other to illustrate details of construction;

FIG. 3 is an elevational view of one end of the elongated support element of the fracture splint;

FIG. 4 is a radial elevational view of the support element shown in FIGS. 2 and 3;

FIG. 4a is a perspective view of the traveling block mounted on the support element of FIGS. 2-4;

FIG. 5 is a plan view of a worm gear forming another part of the splint;

FIG. 6 is a plan view of the proximal element of the splint showing a worm mounted thereon and adapted to be placed in mesh with the worm gear;

FIG. 7 is a dorsal elevational view showing a modified form of the traveling block moveable along a modified support element of the splint;

FIG. 8 is a plan view of the traveling block and support element of FIG. 7;

FIG. 9 is a perspective view of a portion of the traveling block of FIGS. 7 and 8.

FIG. 10 is a side elevational view of the forearm, showing distal and proximal incisions and the locations of distal and proximal pins insertable into the incisions;

FIG. 11 is a cutaway view of the forearm, showing the anatomy thereof and the locations of the distal and proximal pins;

FIG. 12 is a schematic view showing the way in which the distal pins are put into place in the index metacarpal;

FIG. 13 shows a guide for marking the position for insertion of the proximal pins and the radius;

FIG. 14 is a view similar to FIG. 12 but showing the way in which the proximal pins are inserted in the radius;

FIG. 15 is a view similar to FIG. 14 but showing the splint of the present invention coupled to the distal and proximal pins and showing the fracture site before alignment of the distal and proximal fragments of the radius;

FIG. 16 is a view similar to FIG. 15 but showing the distal and proximal fragments in proper alignment with each other;

FIG. 17 is a view similar to FIG. 16 but showing the fracture site out of appositional alignment in which the distal fragment is at a location radial to the proximal fragment;

FIG. 18 is a view showing the fracture site out of rotational and appositional alignment, and illustrating the way in which the splint is adjusted to return the fracture site to proper alignment;

FIG. 19 is a view similar to FIG. 18 but showing the proper alignment of the fracture site after adjustment of the splint;

FIG. 20 is a schematic view of the splint superimposed on the forearm showing the effect of adjusting the splint to improve appositional alignment of the fracture site; and FIG. 21 shows the effect on the distal and proximal fragments when the splint is overly adjusted.

The fracture splint which is the subject of the present invention is broadly denoted by the numeral 10 and includes an elongated support or distal element 12 which is in the form of a longitudinally straight bar of one piece construction. The bar is made of a suitable plastic material, such as nylon or Delrin. The bar can be molded or machined and has high strength characteristics to adequately withstand the bending moments placed on it by the various muscles that cross and thereby deform the fracture site. The bar generally has a rectangular cross-section and is provided with a central slot 14 extending therethrough between a pair of opposed flat faces 16 and 18 (FIGS. 2 and 4) the slot terminating near the distal end 12a and at a location spaced from the proximal end 22 of support element 12.

An elongated rack 24 is provided on a third side face 26 (FIG. 2) of support element 12. Rack 24 has a plurality of spaced teeth which are in mesh with a worm 28 carried by a traveling block 30 on support element 12 for movement longitudinally of the support element in opposed directions.

Shiftable member 30 is in the form of a block as shown in FIG. 4a. The block is typically of the same material as support element 12 and the block has a passage 32 therethrough for slideably receiving support element 12. Traveling block 30 also has a pair of parallel, pin-receiving holes 34 therethrough which are aligned with slot 24 in support element 12. Holes 34 are adapted to receive pins which are adapted to couple the splint 10 to the distal fragment of the radius. Set screws 35 are used to lock the pins in place.

Worm 28 is journalled at its ends in traveling block 30, and the worm extends along and partially projects into opening 32. Also, the worm is in coupled relationship with rack 24 so that, upon rotation of the worm, such as by a tool coupled with a head 29 (FIG. 4) of the worm, traveling block 30 will be caused to advance in one direction or the other along the length of support element 12 depending upon the direction of rotation of the worm. Thus, the positions of holes 34 longitudinally along support element 12 can be adjusted as needed or desired.

The proximal end of support element 12 has an inclined face 40 from which a cylindrical mounting member 42 projects. The mounting member 42 partially extends into a crescent shaped recess 44 formed by a concave inner face 46 (FIG. 3) at the end of support element 12, the axis of the concavity being coincident with the axis 42a of mounting member 42. A pair of side rails 48 (FIGS. 2-4) extend along surface 16 of support element 12 in a direction away from the distal end thereof as shown in FIG. 4. Rails 48 are integral with support element 12 and define a space 50 therebetween for receiving an extension 52 of a worm gear member 54 having a normally inclined worm gear 56 integral with extension 52 as shown in FIGS. 2 and 5. Worm gear 56 has a central hole 58 therethrough and a plurality of gear teeth 60 on a portion of its outer periphery remote from extension 52 as shown in FIG. 5.

Worm gear member 54 is adapted to be rotatably coupled to a cylindrical end part 61 on an inclined face 62 of a proximal end element 63. Element 63 has a convex end face 64 which is adapted to be complementally received with the concave recess 46 (FIG. 3) partially surrounding mounting member 42. Element 63 has a bore 65 extending into an inclined face 67 thereof and the bore is adapted to rotatably receive mounting member 42, whereby block 63 can rotate about the axis 42a of mounting member 42 relative to support element 12.

End part 61 is adapted to be rotatably received within the hole 58 of gear 56 when extension 52 is secured by screws 53 to support element 12 between rails 48, the screws 53 being received in threaded holes 55 in space 50.

A worm 70 is journalled at the ends thereof as shown in FIG. 6 on element 63, the worm being in mesh with the teeth 60 of worm gear 56 when end part 61 is rotatably received in hole 58 of the worm gear. Worm 70 has a tool receiving hole 72 in one end thereof for rotation of the worm in opposed directions relative to element 63. When so rotated, the worm will move relative to the teeth 60 of gear 56. The gear will remain stationary relative to support element 12, and element 63 will rotate about the central axis 42a of mounting member 42.

Element 63 has a first pin receiving hole 74 therethrough, the hole extending at an angle to the central axis of cylindrical end part 61 as shown in FIG. 2. A set screw 76 is used to bear against a pin in hole 74 to releasably lock the pin in place.

A second pin receiving hole 78 extends parallel to hole 74 near the outer or proximal end of the element 63 as shown in FIGS. 2 and 6. A set screw 80 is used to lock a pin in hole 78.

A modification of the traveling block on support element 12 is show in FIGS. 7-9 and is broadly denoted by the numeral 82 and includes a worm 83 which is in mesh with a rack 84 at one side of support element 12 to allow for shiftable movement of member 82 relative to support element 12 in opposed directions. The difference between traveling blocks 30 and 82 lies in the way in which a pair of pin-receiving holes are provided for the respective blocks. As shown in FIG. 4, holes 34 are provided directly in traveling block 30. In contrast, a first hole 85 (FIGS. 7 and 8) is formed by a tubular shaft 89 which extends through shiftable member 82 and through slot 24 of support element 12. The opposite end of tubular shaft 89 is threaded into a sleeve 90 rigid to a wing nut 91 which bears against and is rotatable relative to an adjacent end face of traveling block 82. The sleeve is fixed in place in the traveling block by a set screw 90a (FIG. 7) but is rotatable relative thereto, so that the tubular shaft can be shifted axially relative to the traveling block. The wing nut thereby allows adjustment in the distance d (FIG. 7) between support element 12 and the outer end of an arm 87 through which a second hole 86 extends, arm 87 being rigid to and extending outwardly from the adjacent end 88 of tubular shaft 89.

Tubular shaft 89 also passes through a hole 93 in a triangularly shaped member 94 having a slot 95 as shown in FIGS. 8 and 9. Member 94 is rotatable relative to traveling block 82 about the central axis of tubular member 89, and a sleeve 96 (FIG. 7) having a head 97 passes through slot 95 and into and through slot 24. A set screw 98 is used to tighten head 97 against member 94 so as to adjustably fix member 94 in any one of a number of angular positions relative to traveling block 82, thereby the angle between the plane of arm 87 and the plane of slot 24.

Tubular shaft 89 has flats on the opposed sides thereof for engaging the flat sides of member 94 which define the hole 93 thereof. Thus, rotation of member 94 relative to traveling block 82 will cause pivotal movement of arm 87 about the axis of tubular shaft 89. Pins extending through holes 85 and 86 are held therein by set screws 85a and 86a, respectively.

Splint 10 is configured as shown in FIG. 1 such that the angular adjustment between support element 12 and proximal end element 63 is achieved by manipulation of worm 70 with a central portion of worm gear 56 configured to allow one of the pins to go through it and into the proximal fragment of the radius. Another feature of the invention is the fact that the entire distal portion of support element 12 is made from plastic. This feature allows x-rays to be used with splint 10 since the x-rays pass easily through the plastic material so as to render the fracture site visible in x-ray photographs.

The two major adjustments available with splint 10 are the adjustments available with worm 70 and the shiftability of traveling block 30 (or member 82) on distal portion or support element 12. The worm allows the proximal end element 63 to rotate with respect to the distal portion or support element 12 and, in so doing, allows the distal portion of the device to carry the hand (FIG. 1), the wrist and the distal fragment of the radius about an arc with respect to the proximal fragment of the radius and its attached portion of the splint. This movement is capable of simultaneously improving both rotation and appositional alignment at the fracture site. The major advance provided by splint 10 is the way in which it biomechanically complements the pathomechanics of the Colles' fracture by selectively controlling and reducing the deformity about an axis that is substantially similar to the axis about which the deformity is evolved.

With the use of shiftable member 30 as shown in FIGS. 1, 2 and 4, splint 10 lacks an ability to shift the hand and thereby the distal fragment of the fracture in a radial or ulnar direction if x-rays show that the alignment is not ideal. With the traveling block 82 of FIGS. 7-9, the splint has the ability to selectively move the hand and thereby the wrist and distal fragment in a radial and ulnar direction by manipulation of wing nut 91. Also, traveling block 82 has a feature that allows for selective extension and flexion of the wrist. This feature is provided by the triangular member 94 shown in FIGS. 8 and 9.

FIGS. 10-20 illustrate various aspects of the forearm and fracture site of the radius and the way in which splint 10 is used on the forearm. For instance, FIG. 10 shows the radial aspect of the forearm and the locations of the incisions 100 and 102. FIG. 10 further shows the radial nerve 101 that is to be avoided by pin 103 in incision 100 and pins 104 in incision 102. The ECRL (extension carpi radialis longus) tendon 105 inserts into the radial base of the index metacarpal adjacent to the incision 100; thus, this tendon provides a suitable landmark for the distal pins as the proximal pin of this set typically passes through this tendon and into the index metacarpal.

FIG. 11 illustrates the pertinent anatomy of the forearm and shows the distal and proximal pins 103 and 104 in place. The proximal pins 104 should properly go in the bare portion of the radius which, with minimal dissection, is exposed by retracting the brachioradialis (BR) volarly and the by retracting the abductor pollicis longus (APL) and extensor pollicis brevis (EPB) dorsally, thereby exposing the radial shaft at and just distal to the pronator teres (PT).

FIG. 12 shows the insertion of a second pin 103 into the index metacarpal 108 after a first pin 103 has been inserted into the radial base of the index metacarpal. This is done with the use of a hand-held drill guide 110 having a short barrel 112 which guides the pins 103 into the index metacarpal. Also, the insertion of the pins is accomplished without wrapping up the radial nerve. The aim point 114 of barrel 112 for inserting the first pin 103 is the distal shaft of the little finger metacarpal 116, and the pin is driven through the bases of index metacarpal 108 and the long finger metacarpal 118 adjacent thereto.

Each pin 103 is provided with a pair of spaced index marks 120 as shown in FIG. 12 for use in determining the depth of penetration of the pin. This is an important feature from the viewpoint of the patient because each pin is installed from the radial aspect of the forearm with the pins passing directly ulnarwardly in such a way that they do not nail or otherwise impair the gliding motion of any of the muscle tendons that are necessary for proper hand function. This is further important because the pins typically are in place for two months.

The second distal pin 103 is driven into the shaft of the index metacarpal 108 and this pin is drilled through both cortices and extends just slightly beyond that bone. The first drilled pin 103 extends through a second hole in the drill guide 110 while the second pin is put into place. An additional important feature, from the viewpoint of maintaining hand function while the fracture is healing, is that the pins are installed from the radial aspect of the hand and forearm by means and along a surgical path that does not penetrate or otherwise impair the gliding motion of any of the extrinsic muscle tendon units that pass from the forearm across the wrist and into the hand. In doing so, it helps to preserve motion of the digits and thereby minimizes the risks for permanent hand stiffness.

FIG. 13 shows the use of a marking guide 122 for marking the location for placement of the proximal pins 104 (FIG. 10). The guide 122 has an ulnar plate 123 attached to one side of a leg 124 of a thin, rigid, member 125 having also a second leg 126 and a third leg 127. Leg 126 is perpendicular to leg 124 and leg 127 is at an acute angle with reference to leg 126. Leg 124 has a groove 128 extending along the same for alignment with the ulna head 129 when the ulnar plate 123 is placed on the subcutaneous border of the ulna on the forearm.

A radial guide block 130 is shiftably mounted on the outer end of leg 127 and slideably carries a slotted guide plate 131 having a pair of parallel slots 132 through which a marking pin 133 can extend for marking guide lines on the forearm. Once guide 122 is on the forearm, the guide block 130 is moved until guide plate 131 touches the skin on the forearm. Then, two lines are marked on the skin with the marking pin 133 and the lines indicate the planes into which the proximal pins 104 are to be placed on the radial shaft.

FIG. 14 shows the distal pins 103 in place in the metacarpals of the hand distal to the fracture site 135. FIG. 14 shows placement of the tubular guides of the proximal drill guide such that the legs of the same and therefore the proximal pins will be perpendicular to the shaft of the radius. The second pin is then drilled through the proximal part of the proximal drill guide such that you have a set of properly spaced pins each of which is parallel to the other and perpendicular to the radial shaft. Note that they are drilled from radial to ulnar in a plane formed by the two forearm bones. In FIG. 15, the splint is installed on the two sets of pins by ulnarly deviating the hand on the forearm such that the distal set of pins becomes parallel to the proximal set of pins. A gap of about 2 cm. between the splint and the forearm allows for forearm swelling following surgery such that the skin does not engage the splint itself.

Once the splint 10 is mounted on the distal and proximal pins, the various set screws are tightened to secure the pins to the splint. After the placement of the splint on the pins, the first step is usually to distract the fracture splint such that the overall length between the two sets of pins is increased, restoring appropriate length to the fractured radius by transmitting traction forces to the proximal and distal fragments. This is shown in the change of the fragments from FIG. 15 to FIG. 16. This is accomplished by moving the traveling block 30 axially of the distal portion or support element 12 and away from the proximal pins 104. FIG. 15 shows the distal fragment 137 overlapping the proximal fragment 139 of the radius. After distraction by rotating worm 28 of traveling block 30 as shown in FIG. 16, the length of the radius is restored. It is important that the radius not be overly distracted. Thus, there should be no gap between the distal fragment and the proximal fragment of the radius.

It is possible for the fracture site 135 to be out of appositional alignment in which the distal fragment is positioned radial to the proximal fragment as shown in FIG. 17. In such a case, distal pins 103 are loosened relative to the splint and the hand is pushed ulnarwardly, thereby increasing the gap between the splint and hand so as to realign the distal fragment with respect to the proximal fragment, thereby bringing the distal and proximal fragments back into alignment as shown in FIG. 16.

In the case of the fracture site being out of appositional alignment in the opposite direction, wherein the distal fragment is ulnar with respect to the proximal fragment, the forearm should be displaced away from splint 10, thereby realigning the fractured radius. Then, the pins are again rigidly secured by the set screws to the splint body. With the sliding block 82 as shown in FIGS. 7-9, there is provided an adjustment which will selectively displace the hand and thereby the wrist and distal fragment either radially or ulnarwardly with respect to the forearm. Thus, the structure shown in FIGS. 7-9 provides a selective means to improve appositional alignment in the AP projection by the wing nut 91.

FIG. 18 shows splint 10 coupled to the forearm with the distal fragment out of rotational and appositional alignment with the proximal fragment. The distal fragment and the proximal fragment must be moved relative to each other by adjustment of splint 10 so that the fragments are moved into alignment with each other as shown in FIG. 19. To move the distal fragment back into alignment with the proximal fragment, the worm 70 is rotated by a tool to thereby rotate proximal end element 63 about the pivot axis 42a (FIGS. 2 and 18) relative to support element 12. This movement carries the hand and thereby the wrist and distal fragment through an arc that is capable of simultaneously improving both rotational and appositional alignment of the fracture site at the same time. The important aspect of this feature of splint 10 is the appositional alignment as appreciated from the lateral projection or lateral view such that, when looking into the radial side of the forearm and hand, it is possible to see the effect of the adjustment of the worm gear as depicted in FIG. 20.

FIG. 20 shows the way in which, by adjusting worm 70, the distal fragment is moved into appositional alignment with the proximal fragment. FIG. 20 shows counterclockwise rotation of worm gear 56 as resulting in volar displacement of the distal fragment 137 as indicated by the arrow 140. It is possible to move the distal fragment too far as shown in FIG. 21 wherein the distal fragment is shown as being positioned volarly with respect to the proximal fragment 139. By adjusting the traveling block 30 along the length of support element 12, the length of the radius is restored to normal as the degree of fracture fragment overriding is reduced. Care must be taken to avoid distraction at the fracture site which may lead to delayed or nonunion.

With respect to the modified traveling block 82 of FIGS. 7-9, it is noted that the arm 87 is preferably designed to accommodate two distal pins, one which is about ⅛ inch in diameter and the other about 3/32 inch in diameter. These two pins extend into the radial aspect of the index metacarpal and give adequate purchase with which to flex or extend the hand and thereby the wrist on the forearm.

The mechanism for selective extension or flexion of the wrist is shaft 89 coupled with triangular member by virtue of the flat sided hole 93 as shown in FIG. 9. In addition, selective radial and ulnar displacement of the hand and, therefore, the distal fragment of the radius with respect to the forearm and proximal fragment of the radius is permitted by rotation of wing nut 91 which moves arm 87 and its associated skeletal fixation pins 104 in and out of traveling block 82. All of this is possible in a design that allows the traveling block to be moved along the rack such that worm 83 can give selective distraction to restore length to the fracture site. The important feature about this mechanism is that the wing nut extend through support element 12 while the traveling block is movable along the rack such that worm 83 can give selective distraction to restore length to the fracture at the fracture site while flexion and extension of the hand can occur.

Instead of using a travelling block on support element 12, the support element itself could have selectively adjustable means for increasing or decreasing the distance between the distal (metacarpal) set of pins and the proximal (radial) set of pins. This could be any suitable telescoping or sliding means which is still competent to transmit torsional loads.

What is claimed is:

1. A fracture splint comprising: an elongated first element having block means shiftably mounted thereon near one end thereof for securing first pin means thereto, the first pin means adapted to be inserted into a bone of a patient on one side of a bone fracture; a second element pivotally mounted on said first element near the opposite end thereof for movement of the second element about an axis extending at an angle relative to and in the plane of the longitudinal axis of the first element, the second element having means thereon for securing second pin means thereto, the second pin means adapted to be inserted into the bone of the patient on the opposite side of said bone fracture, the pivotal movement of the second element relative to the first element being the only degree of freedom of the second element relative to the first element.

2. A fracture splint as set forth in claim 1, wherein said securing means for said first pin means worm means thereon for moving the same in opposed directions along the length of the first element.

3. A fracture splint as set forth in claim 2, wherein said moving means comprises a worm and a rack, the worm being in mesh with the teeth of the rack.

4. A fracture splint as set forth in claim 3, wherein the rack is mounted on said first element, said worm being coupled to said securing means for said first pin means.

5. A fracture splint as set forth in claim 1, wherein said block means for the first pin means comprises a block shiftably mounted on the first element for movement in opposed directions, and means coupled with the first element and the block for selectively moving the block along the length of the first element.

6. A fracture splint as set forth in claim 5, wherein said block has a central passage therethrough, said first element being complementally received within and extending through said passage.

7. A fracture splint as set forth in claim 5, wherein said moving means comprises a rack and worm in mesh with the rack.

8. A fracture splint as set forth in claim 7, wherein the rack is carried by the first element and the worm is carried on the block.

9. A fracture splint as set forth in claim 7, wherein the first element has a number of sides, said rack being on one of the sides.

10. A fracture splint as set forth in claim 9, wherein said block has a pin-receiving hole extending therethrough, said first element having a slot extending longitudinally thereof for permitting a pin in the hole of the block to pass through and be moveable through the slot longitudinally of the first element.

11. A fracture splint as set forth in claim 10, wherein is included a set screw carried by the block for releasably locking a pin in said hole of the block.

12. A fracture splint as set forth in claim 1, wherein there is provided gear means coupled to the first element and the second element for pivoting the second element relative to the first element.

13. A fracture splint as set forth in claim 12, wherein said pivoting means comprises a worm and a worm gear.

14. A fracture splint as set forth in claim 13, wherein said worm gear is carried by the first element and the worm is rotatably mounted on the second element, the worm being in mesh with the worm gear.

15. A fracture splint as set forth in claim 1, wherein said first element has an elongated mounting member rigidly secured thereto near said opposite end thereof, said mounting member being at an acute angle with respect to the longitudinal axis of the first element, said second element being pivotally mounted on said mounting member.

16. A fracture splint as set forth in claim 15, wherein said mounting member is cylindrical, said second element having a recess complementally receiving the mounting member on the first element, whereby the second element is rotatable about said axis relative to the first element.

17. A fracture splint as set forth in claim 1, wherein there is included a ring gear secured to said first element and having a central axis coincident with the axis of pivotal movement of the second element relative to the first element, the second element having a worm journalled therein and in mesh with the ring gear.

18. A fracture splint as set forth in claim 17, wherein the ring gear has a central hole therethrough, said second element having a cylindrical part extending into the hole of the ring gear and being rotatable relative thereto.

19. A fracture splint as set forth in claim 18, wherein said cylindrical part of said second element has a pin receiving hole therethrough.

20. A fracture splint as set forth in claim 1, wherein said block means for the first pin includes a block shiftably mounted on the first element for movement longitudinally thereof, there being means on the block for defining a pair of pin-receiving holes.

21. A fracture splint as set forth in claim 20, wherein the block has a pair of aligned side walls on opposite sides of the first element, said holes extending through said side walls.

22. A fracture splint as set forth in claim 20, wherein said defining means on the first element is mounted on the block and movable relative thereto, and means coupled with the defining means on said first element for adjustably moving the same relative to the block.

23. A fracture splint as set forth in claim 22, wherein said defining means on the first element includes a tubular shaft, said moving means including sleeve structure adjustably coupled to the tubular shaft.

24. A fracture splint as set forth in claim 23, wherein said sleeve structure includes a sleeve carried by the block in a fixed location and being rotatable relative to the block, said tubular shaft extending into the sleeve and being threadably coupled thereto.

25. A fracture splint as set forth in claim 24, wherein the sleeve has a wing nut thereon at one end thereof, the wing nut being exteriorly of the block to permit manual rotation of the sleeve and thereby axial movement of the tubular shaft relative to the block.

26. A fracture splint as set forth in claim 23, wherein is included an arm secured to and extending laterally from one end of the tubular shaft, the arm having a pin-receiving hole therein substantially parallel with said tubular shaft.

27. A fracture splint as set forth in claim 26, wherein the tubular shaft and the arm have set screws for releasably securing pins thereto.

28. A fracture splint as set forth in claim 22, wherein is included means for adjustably rotating the defining means on said first element relative to the block, and means coupled with the defining means on said first element for releasably holding the same in any one of a number of rotative positions relative to the block.

29. A fracture splint as set forth in claim 28, wherein said defining means on said first element includes a tubular shaft, said adjustable rotating means includes a rotative member adjacent to the block and coupled with the tubular shaft to permit rotation of the tubular shaft about its longitudinal axis and longitudinal movement of the tubular shaft along its axis.

30. A fracture splint as set forth in claim 29, wherein said rotative member has a rigid, flat body adjacent to one side of the block, said body having a hole therethrough for shiftably receiving the tubular shaft, and tab means on the body for permitting manual rotation of it relative to the block.

31. A fracture splint as set forth in claim 30, wherein the tubular shaft has a flat side, said hole in the body being complemental to the tubular shaft.

32. A fracture splint as set forth in claim 30, wherein said body has an arcuate slot therethrough, said holding means includes an elongated hold-down element shiftably carried by the block and extending through the slot, said hold-down element being frictionally engageable with the body for releasably locking the body to said block.

33. A fracture split as set forth in claim 1, wherein said means on the second element includes structure for mounting a pair of spaced second pins thereon, the second pins being substantially coplanar with said axis of pivoting movement when the pins are mounted by said structure.

34. A fracture splint as set forth in claim 1, wherein said block means on the first element is mounted thereon and movable relative thereto in a direction transverse to the longitudinal axis thereof, and means coupled with the block means on said first element for adjustably moving the same relative to the first element.

35. A fracture splint as set forth in claim 34, wherein said block means on the first element includes a tubular shaft, said moving means including sleeve structure adjustably coupled to the tubular shaft.

36. A fracture splint as set forth in claim 35, wherein said sleeve structure includes a sleeve carried by the first element in a fixed location and being rotatable relative to the first element, said tubular shaft extending into the sleeve and being threadably coupled thereto.

37. A fracture splint as set forth in claim 36, wherein the sleeve has a wing nut thereon at one end thereof, the wing nut being at a location to permit manual rotation of the sleeve and thereby axial movement of the tubular shaft relative to the first element.

38. A fracture splint as set forth in claim 35, wherein is included an arm secured to and extending laterally from one end of the tubular shaft, the arm having a pin-receiving hole therein substantially parallel with said tubular shaft.

39. A fracture splint as set forth in claim 38, wherein the tubular shaft and the arm have set screws for releasably securing pins thereto.

40. A fracture splint as set forth in claim 34, wherein is included rotative means for adjustably rotating the block means on said first element relative to the first element, and means coupled with the block means on said first element for releasably holding the same in any one of a number of rotative positions relative to the first element.

41. A fracture splint as set forth in claim 40, wherein said block means on said first element includes a tubular shaft, said rotative means includes a rotative member adjacent to the first element and coupled with the tubular shaft to permit rotation of the tubular shaft about its longitudinal axis and longitudinal movement of the tubular shaft along its axis.

42. A fracture splint as set forth in claim 41, wherein said member has a rigid, flat body adjacent to one side of the first element, said body having a hole therethrough for shiftably receiving the tubular shaft, and tab means on the body for permitting manual rotation of it relative to the first element.

43. A fracture splint as set forth in claim 42, wherein the tubular shaft has a flat side, said hole in the body being complemental to the tubular shaft.

44. A fracture splint as set forth in claim 42, wherein said body has an arcuate slot therethrough, said holding means includes an elongated hold-down element shiftably carried by the first element and extending through the slot, said hold-down element being frictionally engageable with the body for releasably locking the body to said first element.

* * * * *